(12) United States Patent
Podhajsky et al.

(10) Patent No.: US 8,128,622 B2
(45) Date of Patent: *Mar. 6, 2012

(54) ELECTROSURGICAL PENCIL HAVING A SINGLE BUTTON VARIABLE CONTROL

(75) Inventors: Ronald J Podhajsky, Boulder, CO (US); Dale Francis Schmaltz, Fort Collins, CO (US); Arlan James Reschke, Boulder, CO (US)

(73) Assignee: Covidien AG (CH)

( * ) Notice: Subject to any disclaimer, the term of this patent is extended or adjusted under 35 U.S.C. 154(b) by 1196 days.

This patent is subject to a terminal disclaimer.

(21) Appl. No.: 11/825,821

(22) Filed: Jul. 9, 2007

(65) Prior Publication Data

US 2007/0260239 A1    Nov. 8, 2007

Related U.S. Application Data

(62) Division of application No. 10/701,796, filed on Nov. 5, 2003, now Pat. No. 7,244,257.

(60) Provisional application No. 60/424,352, filed on Nov. 5, 2002.

(51) Int. Cl.
*A61B 18/18* (2006.01)
(52) U.S. Cl. ............................. 606/47; 606/41; 606/49
(58) Field of Classification Search .................. 606/41, 606/42, 45, 46, 48, 49, 50
See application file for complete search history.

(56) References Cited

U.S. PATENT DOCUMENTS

| | | |
|---|---|---|
| 2,031,682 A | 2/1936 | Charles et al. |
| 2,102,270 A | 12/1937 | Hyams |
| 2,993,178 A | 7/1961 | Burger |
| 3,058,470 A | 10/1962 | Seeliger et al. |
| 3,219,029 A | 11/1965 | Richards et al. |
| 3,460,539 A | 8/1969 | Anhalt, Sr. |
| 3,494,363 A | 2/1970 | Jackson |
| 3,648,001 A | 3/1972 | Anderson et al. |
| 3,675,655 A | 7/1972 | Sittner |
| 3,699,967 A | 10/1972 | Anderson |
| 3,720,896 A | 3/1973 | Beierlein |
| 3,801,766 A | 4/1974 | Morrison, Jr. |
| 3,801,800 A | 4/1974 | Newton |
| 3,825,004 A | 7/1974 | Durden, III |
| 3,828,780 A | 8/1974 | Morrison, Jr. |
| 3,875,945 A | 4/1975 | Friedman |
| 3,902,494 A | 9/1975 | Haberlen et al. |

(Continued)

FOREIGN PATENT DOCUMENTS

DE        24 29 021 A1    1/1976

(Continued)

OTHER PUBLICATIONS

International Search Report EP 06 005 540.7 dated Sep. 24, 2007.

(Continued)

*Primary Examiner* — Roy Gibson

(57) ABSTRACT

The present disclosure is directed to electrosurgical pencils having variable controls. In one aspect, the electrosurgical pencil, includes an elongated housing, an electrocautery blade supported within the housing and extending distally from the housing, the electrocautery blade being connected to a source of electrosurgical energy, an activation button supported on the housing, the activation button being movable from a first position to at least a subsequent position, and a transducer electrically connected between the activation button and the source of electrosurgical energy. The transducer is configured to transmit an electrical output signal to the electrosurgical energy source correlating to the movement of the activation button. The source of electrosurgical energy correspondingly supplies an amount of electrosurgical energy to the electrocautery blade dependant upon the electrical output signal.

37 Claims, 4 Drawing Sheets

U.S. PATENT DOCUMENTS

| | | |
|---|---|---|
| 3,906,955 A | 9/1975 | Roberts |
| 3,911,241 A | 10/1975 | Jarrard |
| 3,967,084 A | 6/1976 | Pounds |
| 3,974,833 A | 8/1976 | Durden, III |
| 4,014,343 A | 3/1977 | Esty |
| 4,032,738 A | 6/1977 | Esty et al. |
| 4,034,761 A | 7/1977 | Prater et al. |
| 4,038,984 A | 8/1977 | Sittner |
| 4,112,950 A | 9/1978 | Pike |
| D253,247 S | 10/1979 | Gill |
| 4,232,676 A | 11/1980 | Herczog |
| 4,314,559 A | 2/1982 | Allen |
| 4,427,006 A | 1/1984 | Nottke |
| 4,443,935 A | 4/1984 | Zamba et al. |
| 4,459,443 A | 7/1984 | Lewandowski |
| 4,463,234 A | 7/1984 | Bennewitz |
| 4,463,759 A | 8/1984 | Garito et al. |
| 4,492,231 A | 1/1985 | Auth |
| 4,492,832 A | 1/1985 | Taylor |
| 4,545,375 A | 10/1985 | Cline |
| 4,562,838 A | 1/1986 | Walker |
| 4,589,411 A | 5/1986 | Friedman |
| 4,593,691 A | 6/1986 | Lindstrom et al. |
| 4,595,809 A | 6/1986 | Pool |
| 4,606,342 A | 8/1986 | Zamba et al. |
| 4,619,258 A | 10/1986 | Pool |
| 4,620,548 A | 11/1986 | Hasselbrack |
| 4,625,723 A | 12/1986 | Altnether et al. |
| 4,640,279 A | 2/1987 | Beard |
| 4,642,128 A | 2/1987 | Solorzano |
| 4,655,215 A | 4/1987 | Pike |
| 4,657,016 A | 4/1987 | Garito et al. |
| 4,683,884 A | 8/1987 | Hatfield et al. |
| 4,688,569 A | 8/1987 | Rabinowitz |
| 4,701,193 A | 10/1987 | Robertson et al. |
| 4,712,544 A | 12/1987 | Ensslin |
| 4,735,603 A | 4/1988 | Goodson et al. |
| 4,754,754 A | 7/1988 | Garito et al. |
| 4,785,807 A | 11/1988 | Blanch |
| 4,788,977 A | 12/1988 | Farin et al. |
| 4,794,215 A | 12/1988 | Sawada et al. |
| 4,796,623 A | 1/1989 | Krasner et al. |
| 4,803,323 A | 2/1989 | Bauer et al. |
| 4,811,733 A | 3/1989 | Borsanyi et al. |
| 4,827,911 A | 5/1989 | Broadwin et al. |
| 4,827,927 A | 5/1989 | Newton |
| D301,739 S | 6/1989 | Turner et al. |
| 4,846,790 A | 7/1989 | Hornlein et al. |
| 4,850,353 A | 7/1989 | Stasz et al. |
| 4,860,745 A | 8/1989 | Farin et al. |
| 4,862,889 A | 9/1989 | Feucht |
| 4,862,890 A | 9/1989 | Stasz et al. |
| 4,869,715 A | 9/1989 | Sherburne |
| 4,872,454 A | 10/1989 | DeOliveira et al. |
| 4,876,110 A | 10/1989 | Blanch |
| 4,886,060 A | 12/1989 | Wiksell |
| 4,901,719 A | 2/1990 | Trenconsky et al. |
| 4,903,696 A | 2/1990 | Stasz et al. |
| 4,909,249 A | 3/1990 | Akkas et al. |
| 4,911,159 A | 3/1990 | Johnson et al. |
| 4,916,275 A | 4/1990 | Almond |
| 4,919,129 A | 4/1990 | Weber, Jr. et al. |
| 4,921,476 A | 5/1990 | Wuchinich |
| 4,922,903 A | 5/1990 | Welch et al. |
| 4,931,047 A | 6/1990 | Broadwin et al. |
| 4,949,734 A | 8/1990 | Bernstein |
| 4,969,885 A | 11/1990 | Farin |
| 4,986,839 A | 1/1991 | Wertz et al. |
| 4,988,334 A | 1/1991 | Hornlein et al. |
| 5,000,754 A | 3/1991 | DeOliveira et al. |
| 5,011,483 A | 4/1991 | Sleister |
| 5,013,312 A | 5/1991 | Parins et al. |
| 5,015,227 A | 5/1991 | Broadwin et al. |
| 5,026,368 A | 6/1991 | Adair |
| 5,035,695 A | 7/1991 | Weber, Jr. et al. |
| 5,035,696 A | 7/1991 | Rydell |
| 5,046,506 A | 9/1991 | Singer |
| 5,055,100 A | 10/1991 | Olsen |
| 5,071,418 A | 12/1991 | Rosenbaum |
| 5,074,863 A | 12/1991 | Dines |
| 5,076,276 A | 12/1991 | Sakurai et al. |
| 5,088,997 A | 2/1992 | DeLahuerga et al. |
| 5,098,430 A | 3/1992 | Fleenor |
| 5,100,402 A | 3/1992 | Fan |
| 5,108,391 A | 4/1992 | Flachenecker et al. |
| 5,133,714 A | 7/1992 | Beane |
| 5,147,292 A | 9/1992 | Kullas et al. |
| D330,253 S | 10/1992 | Burek |
| 5,154,709 A | 10/1992 | Johnson |
| 5,160,334 A | 11/1992 | Billings et al. |
| 5,162,044 A | 11/1992 | Gahn et al. |
| 5,167,659 A | 12/1992 | Ohtomo et al. |
| 5,178,012 A | 1/1993 | Culp |
| 5,178,605 A | 1/1993 | Imonti |
| 5,190,517 A | 3/1993 | Zieve et al. |
| 5,192,267 A | 3/1993 | Shapira et al. |
| 5,195,959 A | 3/1993 | Smith |
| 5,196,007 A | 3/1993 | Ellman et al. |
| 5,197,962 A | 3/1993 | Sansom et al. |
| 5,199,944 A | 4/1993 | Cosmescu |
| 5,217,457 A | 6/1993 | DeLahuerga et al. |
| 5,224,944 A | 7/1993 | Elliott |
| 5,226,904 A | 7/1993 | Gentelia et al. |
| 5,233,515 A | 8/1993 | Cosman |
| 5,234,428 A | 8/1993 | Kaufman |
| 5,234,429 A | 8/1993 | Goldhaber |
| 5,242,442 A | 9/1993 | Hirschfeld |
| 5,244,462 A | 9/1993 | DeLahuerga et al. |
| 5,246,440 A | 9/1993 | Van Noord |
| 5,254,082 A | 10/1993 | Takase |
| 5,254,117 A | 10/1993 | Rigby et al. |
| 5,256,138 A | 10/1993 | Burek et al. |
| 5,261,906 A | 11/1993 | Pennino et al. |
| 5,269,781 A | 12/1993 | Hewell, III |
| 5,300,087 A | 4/1994 | Knoepfler |
| 5,304,763 A | 4/1994 | Ellman et al. |
| 5,306,238 A | 4/1994 | Fleenor |
| 5,312,329 A | 5/1994 | Beaty et al. |
| 5,312,400 A | 5/1994 | Bales et al. |
| 5,312,401 A | 5/1994 | Newton et al. |
| 5,318,516 A | 6/1994 | Cosmescu |
| 5,318,565 A | 6/1994 | Kuriloff et al. |
| 5,322,503 A | 6/1994 | Desai |
| 5,330,470 A | 7/1994 | Hagen |
| 5,334,183 A | 8/1994 | Wuchinich |
| 5,342,356 A | 8/1994 | Ellman et al. |
| 5,348,555 A | 9/1994 | Zinnanti |
| 5,366,464 A | 11/1994 | Belknap |
| 5,376,089 A | 12/1994 | Smith |
| 5,380,320 A | 1/1995 | Morris |
| 5,382,247 A | 1/1995 | Cimino et al. |
| 5,395,363 A | 3/1995 | Billings et al. |
| 5,399,823 A | 3/1995 | McCusker |
| 5,401,273 A | 3/1995 | Shippert |
| 5,403,882 A | 4/1995 | Huggins |
| 5,406,945 A | 4/1995 | Riazzi et al. |
| 5,409,484 A | 4/1995 | Erlich et al. |
| 5,413,575 A | 5/1995 | Haenggi |
| 5,421,829 A | 6/1995 | Olichney et al. |
| 5,423,838 A | 6/1995 | Willard |
| 5,431,645 A | 7/1995 | Smith et al. |
| 5,431,650 A | 7/1995 | Cosmescu |
| 5,451,222 A | 9/1995 | De Maagd et al. |
| 5,460,602 A | 10/1995 | Shapira |
| 5,462,522 A | 10/1995 | Sakurai et al. |
| 5,468,240 A | 11/1995 | Gentelia et al. |
| 5,472,442 A | 12/1995 | Klicek |
| 5,472,443 A | 12/1995 | Cordis et al. |
| 5,484,398 A | 1/1996 | Stoddard |
| 5,484,434 A | 1/1996 | Cartmell et al. |
| 5,486,162 A | 1/1996 | Brumbach |
| 5,496,314 A | 3/1996 | Eggers |
| 5,498,654 A | 3/1996 | Shimasaki et al. |
| D370,731 S | 6/1996 | Corace et al. |
| 5,531,722 A | 7/1996 | Van Hale |
| 5,549,604 A | 8/1996 | Sutcu et al. |
| 5,561,278 A | 10/1996 | Rutten |

| Patent Number | Kind | Date | Inventor(s) |
|---|---|---|---|
| 5,601,224 | A | 2/1997 | Bishop et al. |
| 5,609,573 | A | 3/1997 | Sandock |
| 5,626,575 | A | 5/1997 | Crenner |
| 5,630,417 | A | 5/1997 | Petersen et al. |
| 5,630,426 | A | 5/1997 | Eggers et al. |
| 5,630,812 | A | 5/1997 | Ellman et al. |
| 5,633,578 | A | 5/1997 | Eggers et al. |
| 5,634,912 | A | 6/1997 | Injev |
| 5,634,935 | A | 6/1997 | Taheri |
| 5,643,256 | A | 7/1997 | Urueta |
| D384,148 | S | 9/1997 | Monson |
| 5,669,907 | A | 9/1997 | Platt, Jr. et al. |
| 5,674,219 | A | 10/1997 | Monson et al. |
| 5,693,044 | A | 12/1997 | Cosmescu |
| 5,693,050 | A | 12/1997 | Speiser |
| 5,693,052 | A | 12/1997 | Weaver |
| 5,697,926 | A | 12/1997 | Weaver |
| 5,702,360 | A | 12/1997 | Dieras et al. |
| 5,702,387 | A | 12/1997 | Arts et al. |
| 5,712,543 | A | 1/1998 | Sjostrom |
| 5,713,895 | A | 2/1998 | Lontine et al. |
| 5,720,745 | A | 2/1998 | Farin et al. |
| D393,067 | S | 3/1998 | Geary et al. |
| 5,749,869 | A | 5/1998 | Lindenmeier et al. |
| 5,765,418 | A | 6/1998 | Rosenberg |
| 5,776,092 | A | 7/1998 | Farin et al. |
| 5,788,688 | A | 8/1998 | Bauer et al. |
| 5,797,907 | A | 8/1998 | Clement |
| 5,800,431 | A | 9/1998 | Brown |
| 5,836,897 | A | 11/1998 | Sakurai et al. |
| 5,836,909 | A | 11/1998 | Cosmescu |
| 5,836,944 | A | 11/1998 | Cosmescu |
| D402,030 | S | 12/1998 | Roberts et al. |
| D402,031 | S | 12/1998 | Roberts et al. |
| 5,843,109 | A | 12/1998 | Mehta et al. |
| 5,846,236 | A | 12/1998 | Lindenmeier et al. |
| 5,859,527 | A | 1/1999 | Cook |
| 5,868,768 | A | 2/1999 | Wicherski et al. |
| 5,876,400 | A | 3/1999 | Songer |
| 5,888,200 | A | 3/1999 | Walen |
| 5,893,848 | A | 4/1999 | Negus et al. |
| 5,893,849 | A | 4/1999 | Weaver |
| 5,893,862 | A | 4/1999 | Pratt et al. |
| 5,913,864 | A | 6/1999 | Garito et al. |
| 5,919,219 | A | 7/1999 | Knowlton |
| 5,928,159 | A | 7/1999 | Eggers et al. |
| 5,938,589 | A | 8/1999 | Wako et al. |
| 5,941,887 | A | 8/1999 | Steen et al. |
| 5,944,737 | A | 8/1999 | Tsonton et al. |
| 5,951,548 | A | 9/1999 | DeSisto et al. |
| 5,951,581 | A | 9/1999 | Saadat et al. |
| 5,954,686 | A | 9/1999 | Garito et al. |
| 5,972,007 | A | 10/1999 | Sheffield et al. |
| 6,004,318 | A | 12/1999 | Garito et al. |
| 6,004,333 | A | 12/1999 | Sheffield et al. |
| 6,004,335 | A | 12/1999 | Vaitekunas et al. |
| 6,010,499 | A | 1/2000 | Cobb |
| 6,022,347 | A | 2/2000 | Lindenmeier et al. |
| 6,045,564 | A | 4/2000 | Walen |
| 6,063,050 | A | 5/2000 | Manna et al. |
| 6,068,603 | A | 5/2000 | Suzuki |
| 6,068,627 | A | 5/2000 | Orszulak et al. |
| 6,070,444 | A | 6/2000 | Lontine et al. |
| 6,071,281 | A | 6/2000 | Burnside et al. |
| 6,074,386 | A | 6/2000 | Goble et al. |
| 6,074,387 | A | 6/2000 | Heim et al. |
| 6,086,544 | A | 7/2000 | Hibner et al. |
| 6,090,123 | A | 7/2000 | Culp et al. |
| 6,099,525 | A | 8/2000 | Cosmescu |
| 6,117,134 | A | 9/2000 | Cunningham et al. |
| 6,139,547 | A | 10/2000 | Lontine et al. |
| D433,752 | S | 11/2000 | Saravia |
| 6,142,995 | A | 11/2000 | Cosmescu |
| 6,146,353 | A | 11/2000 | Platt, Jr. |
| 6,149,648 | A | 11/2000 | Cosmescu |
| 6,156,035 | A | 12/2000 | Songer |
| 6,197,024 | B1 | 3/2001 | Sullivan |
| 6,200,311 | B1 | 3/2001 | Danek et al. |
| D441,077 | S | 4/2001 | Garito et al. |
| 6,213,999 | B1 | 4/2001 | Platt, Jr. et al. |
| 6,214,003 | B1 | 4/2001 | Morgan et al. |
| 6,238,388 | B1 | 5/2001 | Ellman et al. |
| 6,241,723 | B1 | 6/2001 | Heim et al. |
| 6,241,753 | B1 | 6/2001 | Knowlton |
| 6,249,706 | B1 | 6/2001 | Sobota et al. |
| 6,251,110 | B1 | 6/2001 | Wampler |
| 6,257,241 | B1 | 7/2001 | Wampler |
| 6,258,088 | B1 | 7/2001 | Tzonev et al. |
| 6,273,862 | B1 | 8/2001 | Privitera et al. |
| 6,277,083 | B1 | 8/2001 | Eggers et al. |
| 6,286,512 | B1 | 9/2001 | Loeb et al. |
| 6,287,305 | B1 | 9/2001 | Heim et al. |
| 6,287,344 | B1 | 9/2001 | Wampler et al. |
| 6,312,441 | B1 | 11/2001 | Deng |
| 6,325,799 | B1 | 12/2001 | Goble |
| D453,222 | S | 1/2002 | Garito et al. |
| D453,833 | S | 2/2002 | Hess |
| 6,350,276 | B1 | 2/2002 | Knowlton |
| 6,352,544 | B1 | 3/2002 | Spitz |
| 6,355,034 | B2 | 3/2002 | Cosmescu |
| 6,358,281 | B1 | 3/2002 | Berrang et al. |
| 6,361,532 | B1 | 3/2002 | Burek |
| D457,955 | S | 5/2002 | Bilitz |
| 6,386,032 | B1 | 5/2002 | Lemkin et al. |
| 6,395,001 | B1 | 5/2002 | Ellman et al. |
| 6,402,741 | B1 | 6/2002 | Keppel et al. |
| 6,402,742 | B1 | 6/2002 | Blewett et al. |
| 6,402,743 | B1 | 6/2002 | Orszulak et al. |
| 6,402,748 | B1 | 6/2002 | Schoenman et al. |
| 6,409,725 | B1 | 6/2002 | Khandkar et al. |
| 6,413,255 | B1 | 7/2002 | Stern |
| 6,416,491 | B1 | 7/2002 | Edwards et al. |
| 6,416,509 | B1 | 7/2002 | Goble et al. |
| 6,425,912 | B1 | 7/2002 | Knowlton |
| 6,458,122 | B1 | 10/2002 | Pozzato |
| 6,458,125 | B1 | 10/2002 | Cosmescu |
| 6,461,352 | B2 | 10/2002 | Morgan et al. |
| 6,464,702 | B2 | 10/2002 | Schulze et al. |
| 6,471,659 | B2 | 10/2002 | Eggers et al. |
| 6,494,882 | B1 | 12/2002 | Lebouitz et al. |
| 6,500,169 | B1 | 12/2002 | Deng |
| 6,511,479 | B2 | 1/2003 | Gentelia et al. |
| 6,526,320 | B2 | 2/2003 | Mitchell |
| 6,551,313 | B1 | 4/2003 | Levin |
| 6,558,383 | B2 | 5/2003 | Cunningham et al. |
| 6,585,664 | B2 | 7/2003 | Burdorff et al. |
| 6,589,239 | B2 | 7/2003 | Khandkar et al. |
| 6,610,054 | B1 | 8/2003 | Edwards et al. |
| 6,610,057 | B1 | 8/2003 | Ellman et al. |
| 6,616,658 | B2 | 9/2003 | Ineson |
| 6,618,626 | B2 | 9/2003 | West, Jr. et al. |
| 6,620,161 | B2 | 9/2003 | Schulze et al. |
| 6,632,193 | B1 | 10/2003 | Davison et al. |
| 6,652,514 | B2 | 11/2003 | Ellman et al. |
| 6,662,053 | B2 | 12/2003 | Borkan |
| 6,669,691 | B1 | 12/2003 | Taimisto |
| 6,685,701 | B2 | 2/2004 | Orszulak et al. |
| 6,685,704 | B2 | 2/2004 | Greep |
| 6,702,812 | B2 | 3/2004 | Cosmescu |
| 6,710,546 | B2 | 3/2004 | Crenshaw |
| 6,712,813 | B2 | 3/2004 | Ellman et al. |
| 6,719,746 | B2 | 4/2004 | Blanco |
| 6,740,079 | B1 | 5/2004 | Eggers et al. |
| 6,747,218 | B2 | 6/2004 | Huseman et al. |
| D493,530 | S | 7/2004 | Reschke |
| D493,888 | S | 8/2004 | Reschke |
| D494,270 | S | 8/2004 | Reschke |
| D495,051 | S | 8/2004 | Reschke |
| D495,052 | S | 8/2004 | Reschke |
| 6,794,929 | B2 | 9/2004 | Pelly |
| 6,830,569 | B2 | 12/2004 | Thompson et al. |
| 6,840,948 | B2 | 1/2005 | Albrecht et al. |
| 6,855,140 | B2 | 2/2005 | Albrecht et al. |
| 6,902,536 | B2 | 6/2005 | Manna et al. |
| 6,905,496 | B1 | 6/2005 | Ellman et al. |
| 6,923,804 | B2 | 8/2005 | Eggers et al. |
| 6,923,809 | B2 | 8/2005 | Eggers et al. |
| 6,939,347 | B2 | 9/2005 | Thompson |

| | | |
|---|---|---|
| 6,955,674 B2 | 10/2005 | Eick et al. |
| D515,412 S | 2/2006 | Waaler et al. |
| 7,033,353 B2 | 4/2006 | Stoddard et al. |
| D521,641 S | 5/2006 | Reschke et al. |
| D535,396 S | 1/2007 | Reschke et al. |
| 7,156,842 B2 | 1/2007 | Sartor et al. |
| 7,156,844 B2 | 1/2007 | Reschke et al. |
| 7,235,072 B2 | 6/2007 | Sartor et al. |
| 7,241,294 B2 | 7/2007 | Reschke |
| 7,244,257 B2 | 7/2007 | Podhajsky et al. |
| 2001/0047183 A1 | 11/2001 | Privitera et al. |
| 2001/0049524 A1 | 12/2001 | Morgan et al. |
| 2002/0019596 A1 | 2/2002 | Eggers et al. |
| 2002/0019631 A1 | 2/2002 | Kidder et al. |
| 2002/0022838 A1 | 2/2002 | Cunningham et al. |
| 2002/0026145 A1 | 2/2002 | Bagaoisan et al. |
| 2002/0035364 A1 | 3/2002 | Schoenman et al. |
| 2002/0049427 A1 | 4/2002 | Wiener et al. |
| 2002/0058958 A1 | 5/2002 | Walen |
| 2002/0087079 A1 | 7/2002 | Culp et al. |
| 2002/0095199 A1 | 7/2002 | West, Jr. et al. |
| 2002/0103485 A1 | 8/2002 | Melnyk et al. |
| 2002/0111622 A1 | 8/2002 | Khandkar et al. |
| 2002/0133148 A1 | 9/2002 | Daniel et al. |
| 2002/0151886 A1 | 10/2002 | Wood |
| 2002/0151887 A1 | 10/2002 | Stern et al. |
| 2002/0156471 A1 | 10/2002 | Stern et al. |
| 2002/0173776 A1 | 11/2002 | Batchelor et al. |
| 2002/0198519 A1 | 12/2002 | Qin et al. |
| 2003/0004508 A1 | 1/2003 | Morgan et al. |
| 2003/0014043 A1 | 1/2003 | Henry et al. |
| 2003/0032950 A1 | 2/2003 | Altshuler et al. |
| 2003/0050633 A1 | 3/2003 | Ellman et al. |
| 2003/0055421 A1 | 3/2003 | West et al. |
| 2003/0061661 A1 | 4/2003 | Borders et al. |
| 2003/0065321 A1 | 4/2003 | Carmel et al. |
| 2003/0078572 A1 | 4/2003 | Pearson et al. |
| 2003/0083655 A1 | 5/2003 | Van Wyk |
| 2003/0088247 A1 | 5/2003 | Ineson |
| 2003/0109864 A1 | 6/2003 | Greep et al. |
| 2003/0109865 A1 | 6/2003 | Greep et al. |
| 2003/0130663 A1 | 7/2003 | Walen |
| 2003/0144680 A1 | 7/2003 | Kellogg et al. |
| 2003/0163125 A1 | 8/2003 | Greep |
| 2003/0199856 A1 | 10/2003 | Hill et al. |
| 2003/0199866 A1 | 10/2003 | Stern et al. |
| 2003/0199869 A1 | 10/2003 | Johnson et al. |
| 2003/0212393 A1 | 11/2003 | Knowlton et al. |
| 2003/0212397 A1 | 11/2003 | Avrahami et al. |
| 2003/0216728 A1 | 11/2003 | Stern et al. |
| 2003/0220635 A1 | 11/2003 | Knowlton et al. |
| 2003/0220638 A1 | 11/2003 | Metzger |
| 2003/0225401 A1 | 12/2003 | Eggers et al. |
| 2003/0229341 A1 | 12/2003 | Albrecht et al. |
| 2003/0229343 A1 | 12/2003 | Albrecht et al. |
| 2004/0000316 A1 | 1/2004 | Knowlton et al. |
| 2004/0002704 A1 | 1/2004 | Knowlton et al. |
| 2004/0002705 A1 | 1/2004 | Knowlton et al. |
| 2004/0010246 A1 | 1/2004 | Takahashi |
| 2004/0015160 A1 | 1/2004 | Lovewell |
| 2004/0015161 A1 | 1/2004 | Lovewell |
| 2004/0015162 A1 | 1/2004 | McGaffigan |
| 2004/0015216 A1 | 1/2004 | DeSisto |
| 2004/0024395 A1 | 2/2004 | Ellman et al. |
| 2004/0024396 A1 | 2/2004 | Eggers |
| 2004/0030328 A1 | 2/2004 | Eggers et al. |
| 2004/0030330 A1 | 2/2004 | Brassell et al. |
| 2004/0030332 A1 | 2/2004 | Knowlton et al. |
| 2004/0030367 A1 | 2/2004 | Yamaki |
| 2004/0034346 A1 | 2/2004 | Stern et al. |
| 2004/0054370 A1 | 3/2004 | Given |
| 2004/0111087 A1 | 6/2004 | Stern et al. |
| 2004/0124964 A1 | 7/2004 | Wang et al. |
| 2004/0127889 A1 | 7/2004 | Zhang et al. |
| 2004/0143677 A1 | 7/2004 | Novak |
| 2004/0147909 A1 | 7/2004 | Johnston et al. |
| 2004/0162553 A1 | 8/2004 | Peng et al. |
| 2004/0167512 A1 | 8/2004 | Stoddard et al. |
| 2004/0172011 A1 | 9/2004 | Wang et al. |
| 2004/0172015 A1 | 9/2004 | Novak |
| 2004/0172016 A1 | 9/2004 | Bek et al. |
| 2004/0181140 A1 | 9/2004 | Falwell et al. |
| 2004/0236323 A1 | 11/2004 | Schoenman et al. |
| 2004/0243120 A1 | 12/2004 | Orszulak et al. |
| 2004/0267252 A1 | 12/2004 | Washington et al. |
| 2004/0267254 A1 | 12/2004 | Manzo et al. |
| 2004/0267297 A1 | 12/2004 | Malackowski |
| 2005/0033286 A1 | 2/2005 | Eggers et al. |
| 2005/0059858 A1 | 3/2005 | Frith et al. |
| 2005/0059967 A1 | 3/2005 | Breazeale, Jr. et al. |
| 2005/0065510 A1 | 3/2005 | Carmel et al. |
| 2005/0070891 A1 | 3/2005 | DeSisto |
| 2005/0085804 A1 | 4/2005 | McGaffigan |
| 2005/0096645 A1 | 5/2005 | Wellman et al. |
| 2005/0096646 A1 | 5/2005 | Wellman et al. |
| 2005/0096681 A1 | 5/2005 | Desinger et al. |
| 2005/0113817 A1 | 5/2005 | Isaacson et al. |
| 2005/0113818 A1 | 5/2005 | Sartor et al. |
| 2005/0113824 A1 | 5/2005 | Sartor et al. |
| 2005/0113825 A1 | 5/2005 | Cosmescu |
| 2005/0149001 A1 | 7/2005 | Uchikubo et al. |
| 2005/0154385 A1 | 7/2005 | Heim et al. |
| 2006/0041257 A1 | 2/2006 | Sartor et al. |
| 2006/0058783 A1 | 3/2006 | Buchman |
| 2006/0178667 A1 | 8/2006 | Sartor et al. |
| 2007/0049926 A1 | 3/2007 | Sartor |
| 2007/0093810 A1 | 4/2007 | Sartor |
| 2007/0142832 A1 | 6/2007 | Sartor |

FOREIGN PATENT DOCUMENTS

| | | |
|---|---|---|
| DE | 24 60 481 A1 | 6/1976 |
| DE | 30 45 996 | 7/1982 |
| EP | 0186369 A | 7/1986 |
| EP | 1050277 | 11/2000 |
| EP | 1050279 | 11/2000 |
| EP | 1082945 | 3/2001 |
| EP | 1293171 | 3/2003 |
| EP | 1 645 233 | 4/2006 |
| EP | 1656900 | 5/2006 |
| EP | 1645234 | 12/2006 |
| EP | 1852078 | 11/2007 |
| FR | 2235669 | 1/1975 |
| FR | 2798579 | 3/2001 |
| WO | WO 94/20032 | 9/1994 |
| WO | WO 96/39086 | 12/1996 |
| WO | WO 98/43264 | 10/1998 |
| WO | WO 01/64122 | 9/2001 |
| WO | WO 02/47568 A1 | 6/2002 |
| WO | WO 2004/010883 A1 | 2/2004 |
| WO | WO 2004/045436 A1 | 6/2004 |
| WO | WO 2004/073753 A2 | 9/2004 |
| WO | WO 2005/060849 A1 | 7/2005 |

OTHER PUBLICATIONS

International Search Report from PCT/US03/37111; Jul. 21, 2004.
International Search Report from PCT/US04/04685; Aug. 6, 2004.
International Search Report from EP 04015980; Sep. 30, 2004.
International Search Report from PCT/US03/22900; Nov. 20, 2003.
International Search Report from EP 05019882.9 dated Feb. 16, 2006.
International Search Report from EP 05021777.7 dated Feb. 23, 2006.
International Search Report from EP 06014461.5 dated Oct. 31, 2006.
International Search Report from EP 07009028 dated Jul. 16, 2007.
International Search Report from Application No. EP 06 00 6908 dated Feb. 25, 2009.
International Search Report from Application No. EP 08 02 1070 dated Apr. 1, 2009.
Zucker, Karl, Surgical Laparoscopy, Lippincott Williams & Wilkins, Ed. 2, 2001 (2 pages).

ELECTROSURGICAL PENCIL HAVING A SINGLE BUTTON VARIABLE CONTROL

CROSS-REFERENCE TO RELATED APPLICATIONS

The present application is a Divisional Application which claims the benefit of and priority to U.S. application Ser. No. 10/701,796, filed on Nov. 5, 2003 now U.S. Pat. No. 7,244,257, which claims the benefit of and priority to U.S. Provisional Application Ser. No. 60/424,352 filed on Nov. 5, 2002, the entire contents of each of which are incorporated herein by reference.

BACKGROUND

1. Technical Field

The present disclosure relates generally to electrosurgical instruments and, more particularly, to an electrosurgical pencil having a single button variable control.

2. Background of Related Art

Electrosurgical instruments have become widely used by surgeons in recent years. Accordingly, a need has developed for equipment and instruments which are easy to handle, are reliable and are safe in an operating environment. By and large, most electrosurgical instruments typically include a hand-held instrument, or pencil, which transfers radio-frequency (RF) electrical energy to a tissue site. The electrosurgical energy is returned to the electrosurgical source via a return electrode pad positioned under a patient (i.e., a monopolar system configuration) or a smaller return electrode positionable in bodily contact with or immediately adjacent to the surgical site (i.e., a bipolar system configuration). The waveforms produced by the RF source yield a predetermined electrosurgical effect known generally as electrosurgical fulguration.

In particular, electrosurgical fulguration includes the application of electric spark to biological tissue, for example, human flesh or the tissue of internal organs, without significant cutting. The spark is produced by bursts of radio-frequency electrical energy generated from an appropriate electrosurgical generator. Generally, fulguration is used to either coagulate, cut or seal body tissue. Coagulation is defined as a process of desiccating tissue wherein the tissue cells are ruptured and dehydrated/dried. Electrosurgical cutting, on the other hand, includes applying an electrical spark to tissue in order to produce a cutting effect. Meanwhile, sealing is defined as the process of liquefying the collagen in the tissue so that it forms into a fused mass.

As used herein the term "electrosurgical pencil" is intended to include instruments which have a handpiece which is attached to an active electrode and which is used to coagulate, cut and/or seal tissue. Typically, the electrosurgical pencil may be operated by a handswitch or a foot switch. The active electrode is an electrically conducting element which is usually elongated and may be in the form of a thin flat blade with a pointed or rounded distal end. Alternatively, the active electrode may include an elongated narrow cylindrical needle which is solid or hollow with a flat, rounded, pointed or slanted distal end. Typically electrodes of this sort are known in the art as "blade", "loop" or "snare", "needle" or "ball" electrodes.

As mentioned above, the handpiece of the electrosurgical pencil is connected to a suitable electrosurgical energy source (i.e., generator) which produces the radio-frequency electrical energy necessary for the operation of the electrosurgical pencil. In general, when an operation is performed on a patient with an electrosurgical pencil, electrical energy from the electrosurgical generator is conducted through the active electrode to the tissue at the site of the operation and then through the patient to a return electrode. The return electrode is typically placed at a convenient place on the patient's body and is attached to the generator by a conductive material.

Current electrosurgical instrument systems allow the surgeon to change between two pre-configured settings (i.e., coagulation and cutting) via two discrete buttons disposed on the electrosurgical pencil itself. Other electrosurgical instrument systems allow the surgeon to increment the power applied when the coagulating or cutting button of the instrument is depressed by adjusting or closing a switch on the electrosurgical generator. The surgeon then needs to visually verify the change in the power being applied by looking at various displays and/or meters on the electrosurgical generator. In other words, all of the adjustments to the electrosurgical instrument and parameters being monitored during the use of the electrosurgical instrument are typically located on the electrosurgical generator. As such, the surgeon must continually visually monitor the electrosurgical generator during the surgical procedure.

Accordingly, the need exists for electrosurgical instruments which do not require the surgeon to continually monitor the electrosurgical generator during the surgical procedure. In addition, the need exists for electrosurgical instruments whose power output can be adjusted without the surgeon having to turn his vision away from the operating site and toward the electrosurgical generator.

SUMMARY

The present disclosure is directed to an electrosurgical instrument having variable controls. In accordance with one aspect of the present disclosure the electrosurgical instrument, includes an elongated housing, an electrocautery blade supported within the housing and extending distally from the housing, the electrocautery blade being connected to a source of electrosurgical energy, an activation button supported on the housing, the activation button being movable from a first position to at least a subsequent position, and a transducer electrically connected between the activation button and the source of electrosurgical energy. The transducer is configured to transmit an electrical output signal to the electrosurgical energy source correlating to the movement of the activation button. The source of electrosurgical energy correspondingly supplies an amount of electrosurgical energy to the electrocautery blade dependant upon the electrical output signal.

In one aspect, the activation button is depressed to initiate transmission of the electrical output signal. Preferably, the activation button is movable from a first position to a series of discrete, subsequent positions wherein each subsequent position corresponds to a specific amount of electrosurgical energy being transmitted to the electrocautery blade.

It is envisioned that the transducer is a pressure-sensitive transducer. Preferably, the pressure transducer produces at least two output signals based upon the movement of the activation button. It is further envisioned that one of the at least two signals of the pressure transducer transmits a signal to the electrosurgical generator corresponding to the emission of energy having a cutting-type waveform and the other of the at least two signals of the pressure transducer transmits a signal to the electrosurgical generator corresponding to the emission of energy having a coagulating-type waveform.

Preferably, the pressure transducer transmits a range of output signals to the source of electrosurgical energy in response to the position of the activation button. The range of output signals corresponds to a range of energy emission from the source of electrosurgical energy to the electrocautery blade.

In a further aspect, the activation button includes a slide-switch which is slidingly supported on the housing and is configured for selective movement along a slide path formed in the housing. The transducer is configured to produce an output signal to the source of electrosurgical energy which corresponds to the movement of the slide-switch within the slide path of the housing.

Preferably, the slide-switch transmits a range of output signals to the source of electrosurgical energy in response to the position of the slide-switch, the range of output signals varying from when the slide-switch is at a proximal-most position to when the slide switch is at a distal-most position. The slide-switch is configured and adapted to be depressed to initiate movement thereof and activation of the electrocautery blade.

In another aspect of the present disclosure, the electrosurgical pencil further includes a control pendent operatively coupled to the housing and electrically connected to the source of electrosurgical energy. The control pendent includes at least one control knob operatively supported thereon, wherein the at least one control knob is configured and adapted to enable selection of a particular emission signal from the electrosurgical generator.

Preferably, the at least one control knob is electrically connected to the activation button. It is envisioned that the at least one control knob is electrically connected to the source of electrosurgical energy.

It is contemplated that the control pendent is configured and adapted to be removably attached to at least one of a user's wrist, user's garment and operating table. It is further contemplated that the control pendent includes at least one knob for selecting a function of the electrosurgical instrument and at least one other knob for selecting a power output of the source of electrosurgical energy.

These and other objects will be more clearly illustrated below by the description of the drawings and the detailed description of the preferred embodiments.

BRIEF DESCRIPTION OF THE DRAWINGS

The accompanying drawings, which are incorporated in and constitute a part of this specification, illustrate embodiments of the invention, and together with a general description of the invention given above, and the detailed description of the embodiments given below, serve to explain the principles of the invention.

DETAILED DESCRIPTION

Figure 1:
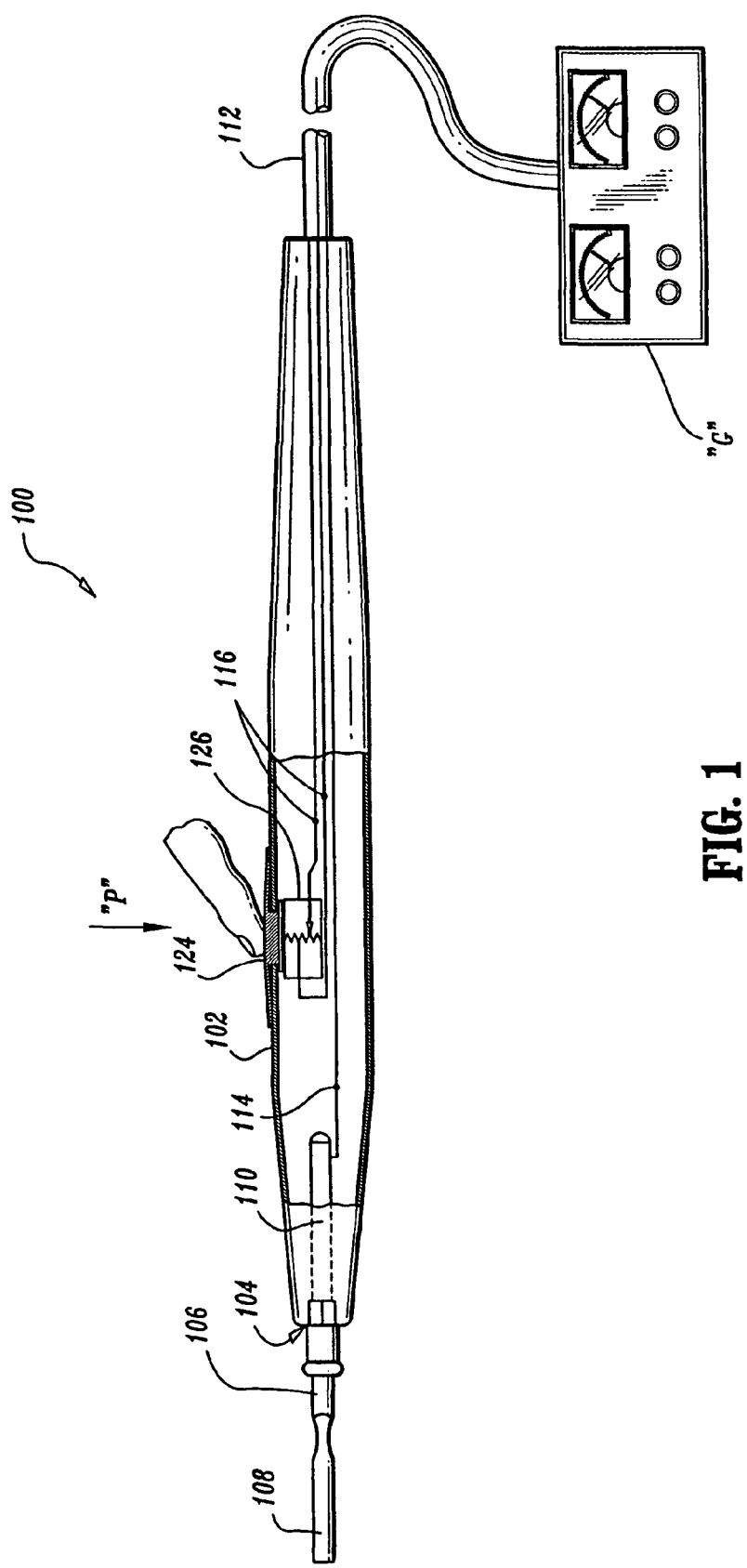
FIG. 1 is a partially broken, side elevational view of one embodiment of an electrosurgical pencil in accordance with the present disclosure.

Embodiments of the presently-disclosed electrosurgical pencil will now be described in detail with reference to the drawing figures wherein like reference numerals identify similar or identical elements. In the drawings, and in the description which follows, the term "proximal", as is traditional, will refer to the end of the electrosurgical pencil which is closest to the operator, while the term "distal" will refer to the end of the electrosurgical pencil which is furthest from the operator.

FIG. 1 sets forth a partially broken, side elevational view of an electrosurgical pencil constructed in accordance with one embodiment of the present disclosure and generally referenced by numeral 100. While the following description will be directed towards electrosurgical pencils it is envisioned that the features and concepts of the present disclosure can be applied to any electrosurgical type instrument. Electrosurgical pencil 100 includes an elongated housing 102 configured and adapted to support a blade receptacle 104 at a distal end thereof which, in turn, receives a replaceable electrocautery blade 106 therein. A distal end portion 108 of blade 106 extends distally from receptacle 104 while a proximal end portion 110 of blade 106 is retained within the distal end of housing 102. Preferably, electrocautery blade 106 is fabricated from a conductive type material, i.e., stainless steel or is coated with an electrically conductive material.

As shown, electrosurgical pencil 100 is coupled to a conventional electrosurgical generator "G" via a cable 112. Cable 112 includes a transmission wire 114 which electrically interconnects the electrosurgical generator "G" with the proximal end portion 110 of blade 106. Cable 112 further includes a control loop 116 which electrically interconnects an activation button 124, supported on an outer surface 107 of the housing 102, with the electrosurgical generator "G".

By way of example only, electrosurgical generator "G" may be any one of the following, or equivalents thereof: the "FORCE FX", "FORCE 2" or "FORCE 4" generators manufactured by Valleylab, Inc. a division of Tyco Healthcare, LP, Boulder, Colo. Preferably, the electrosurgical generator "G" can be variable in order to provide appropriate first RF signals (e.g., 1 to 120 watts) for tissue cutting and appropriate second RF signals (e.g., 1 to 300 watts) for tissue coagulation. Preferably, an exemplary electrosurgical generator "G" is disclosed in commonly assigned U.S. Pat. No. 6,068,627 to Orszulak, et al., the entire content of which are hereby incorporated by reference. The electrosurgical generator disclosed in the '627 patent includes, inter alia, an identifying circuit and a switch therein. In general, the identifying circuit is responsive to information received from a generator and transmits a verification signal back to the generator. Meanwhile, the switch is connected to the identifying circuit and is responsive to signaling received from the identifying circuit.

Turning back to FIG. 1, as mentioned above, electrosurgical pencil 100 includes activation button 124 which is supported on an outer surface 107 of housing 102. Activation button 124 is operatively connected to a pressure transducer 126 (or other variable power switch) which, in turn, controls the RF electrical energy supplied from generator "G" to electrosurgical blade 106. More particularly, pressure transducer 126 electrically couples to control loop 116 and is configured to regulate (or variably control) the amount of RF energy transmitted to electrocautery blade 106 and/or to variably control the waveform output from electrosurgical generator "G".

In use, pressure transducer 126 converts input energy of one form into output energy of another. For example, pressure transducer 126 initially converts a pressure input from activation button into an output signal which is transmitted to electrosurgical generator "G". In turn, generator "G" transmits a corresponding amount of energy (or an appropriate waveform output) to electrocautery blade 106 via transmission wire 114. As such, by selectively applying pressure to switch 124 to apply pressure to pressure transducer 126, the surgeon can variably control the amount of energy and/or the waveform output of the electrosurgical generator "G". For example, by applying a relatively light pressure against activation button 124, and, in turn, to pressure transducer 126, in the direction of arrow "P" in FIG. 1, thus depressing pressure transducer 126 a relatively small amount, a "cutting-type" waveform is transmitted. By applying a relatively heavy pressure against activation button 124, thus depressing pressure transducer 126 a relatively large amount, a "coagulating-type" waveform is transmitted. As can be appreciated, an intermediate pressure applied against activation button 124 will produce varying combinations of "cutting-type" waveforms and "coagulating-type" waveforms.

More particularly and in use, when activation button 124 is depressed in direction "P", pressure is applied against transducer 126 which, in turn, converts the input pressure into a corresponding electrical signal. The electrical signal is transmitted, via control loop 116, to electrosurgical generator "G". Electrosurgical generator "G", in turn, processes the electrical signal received from pressure transducer 126 and transmits an output signal (i.e., RF energy, waveform, power, voltage, current, duty, cycle, frequency and the like), via transmission wire 114, to electrocautery blade 106. As can be appreciated, the pressure "P" applied to activation button 124 against the pressure transducer 126, directly determines the overall level of output of electrosurgical generator "G" and, in turn, the ultimate function of electrocautery blade 106. Since activation button 124 can be depressed to a variety of positions the surgeon is able to create a pallet of varying therapeutic effects ranging from a pure "cutting" mode to a pure "coagulating" mode and variations therebetween. It is envisioned that the switch 124 may include a plurality of incremental steps (not shown) to provide better tactile feedback to the surgeon. It is also contemplated that the incremental steps may include audible feedback to further enhance the surgeon's tactile feedback.

As such, the surgeon need not visually verify the new setting of electrosurgical pencil 100 by continuously checking the display, meters or gauges on electrosurgical generator "G". In particular, the surgeon will be able to make changes to the electrosurgical pencil, as needed, from the operative field.

It is contemplated that activation button 124 can included other electromechanical sensors, e.g., optical sensors, pneumatic sensors, accelerometer, position sensors, etc. to provide sensory feedback to generator "G". As mentioned above, the activation button 124 may also include some measure of tactile feedback which is felt by the surgeon's finger and/or some measure of audible feedback produced by the activation button 124 (e.g., a "click"), by the electrosurgical generator "G" (e.g., a "tone") and/or an auxiliary sound-producing device such as a buzzer (not shown).

While RF energy and waveforms have been disclosed as being controlled by the position of or pressure applied to pressure transducer 126, it is envisioned that other electrosurgical parameters can be controlled by pressure transducer 126, such as, for example, power, voltage, current, duty, cycle and/or frequency.

Figure 2:
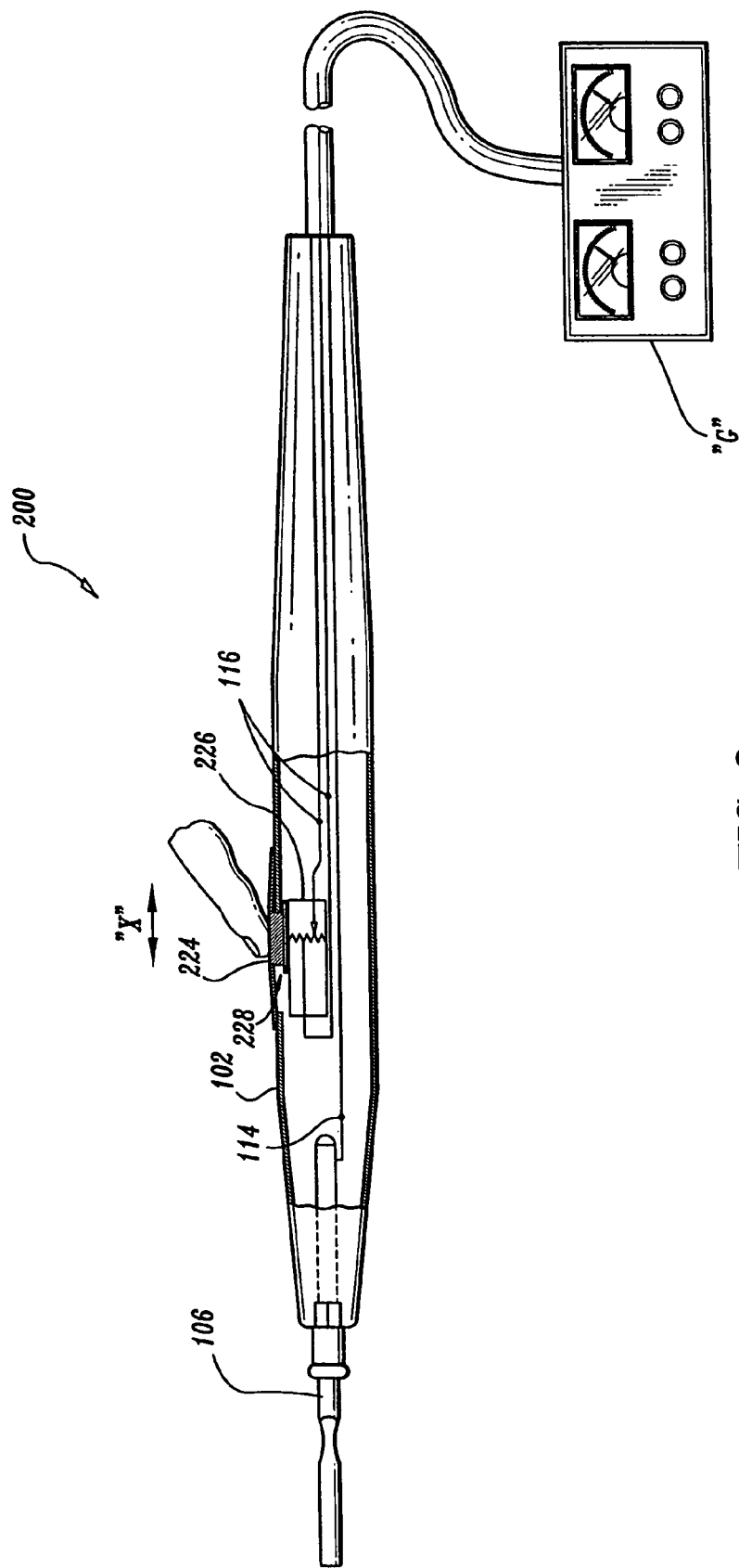
FIG. 2 is a partially broken, side elevational view of an alternate embodiment of the electrosurgical pencil, in accordance with the present disclosure, shown in a first position.
Figure 3:
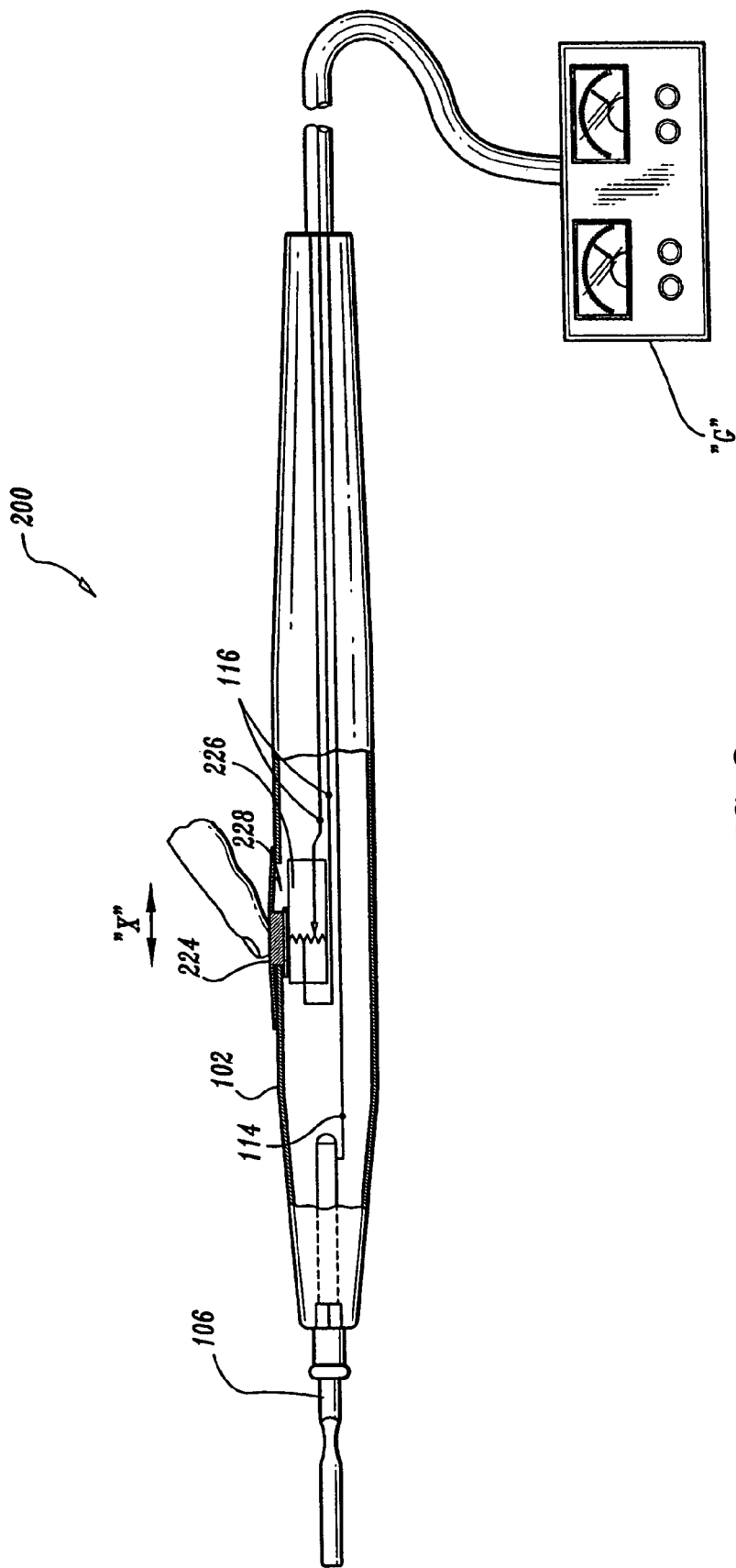
FIG. 3 is a partially broken, side elevational view of the electrosurgical pencil of FIG. 2 shown in a second position.

Turning now to FIGS. 2-3, an alternate electrosurgical pencil 200 is shown and includes a slide-switch 224 which is slidably supported atop a slide bed 228 disposed within the outer surface 107 of housing 102. Preferably, slide-switch 224 is operatively connected to transducer 226 which is, in turn, electrically connected to control loop 116 in a similar manner as described above.

In the present embodiment, as slide-switch 224 is displaced, either proximally or distally along activation line "X", transducer 226 converts the degree of displacement of slide-switch 224 into a signal which is transmitted to electrosurgical generator "G" via transmission line 116. Generator "G", in turn, transmits a corresponding amount of RF energy (or an appropriate waveform output) to electrocautery blade 106. As such, slide-switch 224, in combination with transducer 226, allows the surgeon to variably control the amount of energy and/or the waveform output of electrosurgical generator "G". For example, when slide-switch 224 is in a proximal-most position, as seen in FIG. 2, a "cutting-type" waveform is selected. Meanwhile, by displacing slide-switch 224 to a distal-most position, as seen in FIG. 3, a "coagulating-type" waveform is selected. It is envisioned that positioning slide-switch 224 at discrete locations along the length of slide bed 228 will induce a combination of "cutting-type" waveforms and "coagulating-type" waveforms. Accordingly, the surgeon can select the therapeutic effect desired by simply displacing slide-switch 224 to an appropriate position along slide bed 228.

It is envisioned that slide bed 228 may be configured such that slide-switch 224 "clicks" into discrete positions along slide bed 228 from the proximal-most position to the distal-most position. The "clicking" provides the surgeon with both tactile and audible feedback as to the location of slide-switch 224. It is further envisioned that electrosurgical pencil 200 may be activated and deactivated (i.e., energized or de-energized) by depressing and then releasing sliding button 224.

Figure 4:
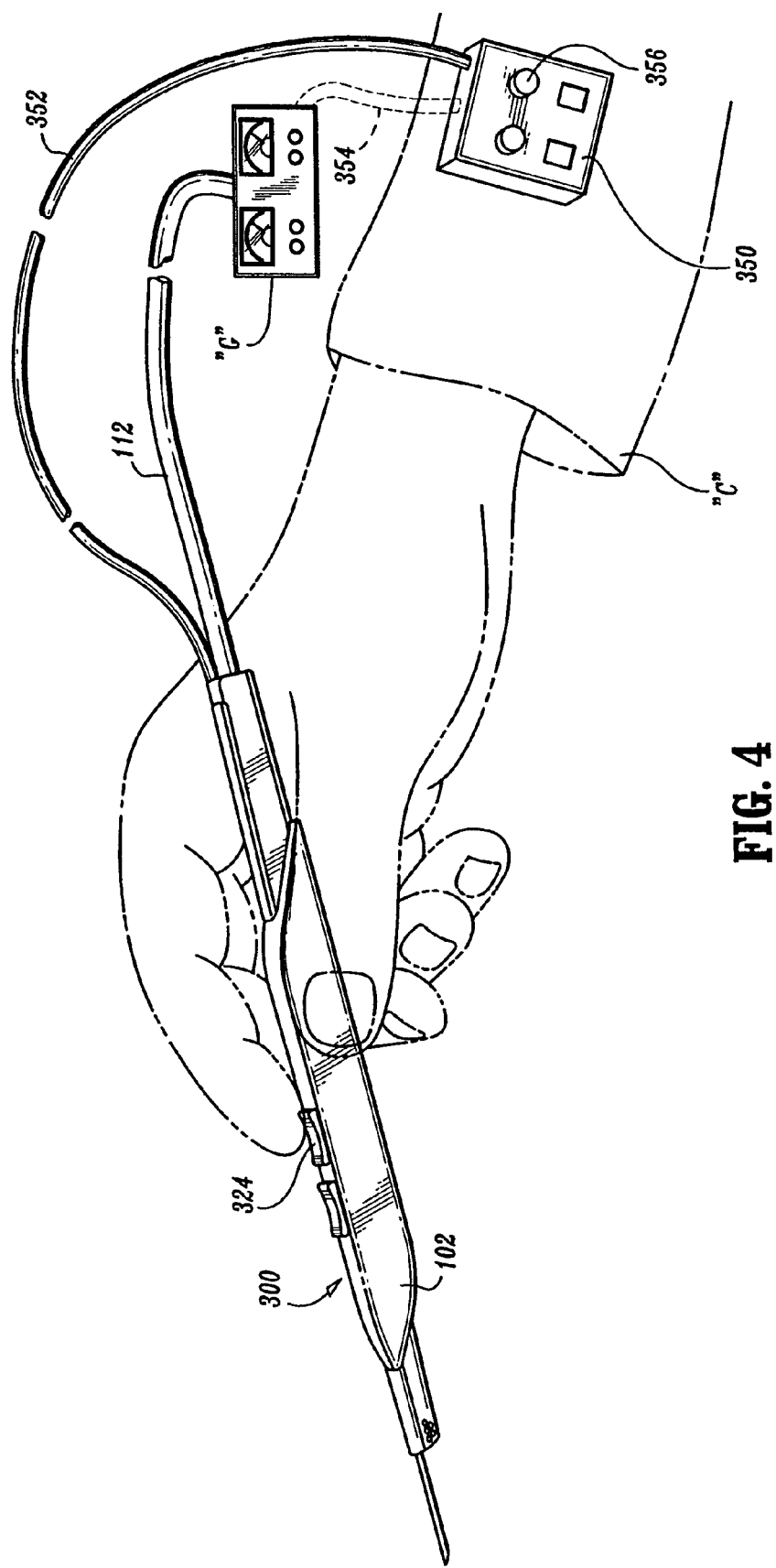
FIG. 4 is a perspective view of another alternate embodiment of an electrosurgical pencil shown being held in the hand of a surgeon (shown in phantom).

Turning now to FIG. 4, an alternate embodiment of an electrosurgical pencil 300 is shown and includes at least one activation button 324 supported on the outer surface 107 of housing 102. It is envisioned that two activation button 324, 325 may also be employed. In accordance with this embodiment, electrosurgical pencil 300 preferably includes a pendent 350 which is configured and adapted to be removably attached to or stuck to the surgeons wrist or coat sleeve "C" (as seen in FIG. 4), the patients drapes or robe, or a Mayo stand. It is envisioned that the pendent 350 may also be removably attached by any known means such as clips, Velcro™, band, belt, elastic, or the like.

As seen in FIG. 4, pendent 350 is electrically connected to electrosurgical pencil 300 via a connecting wire 352. Optionally, pendent 350 can be electrically connected to electrosurgical generator "G" via a connecting wire 354 (shown in phantom in FIG. 4). Pendent 350 preferably includes at least some of, if not all of, the variable controls 356 of electrosurgical pencil 300. Variable controls 356 permit the surgeon to select the function desired (i.e., cutting or coagulating) and to vary the power being supplied by electrosurgical generator "G" to electrosurgical pencil 300. Variable controls 356, include, but are not limited to knobs, buttons, switches, dials, slides, touch screens, etc.

In use, the surgeon can select the function and level of power from pendent 350 instead of electrosurgical generator "G". The surgeon then uses or activates and deactivates electrosurgical pencil 300 in a conventional manner by depressing and releasing activation button 324 or 325. Accordingly, during use of electrosurgical pencil 300, if the surgeon desires to vary or adjust the output or function of electrosurgical pencil 300, the surgeon simply needs to adjust variable controls 356 of pendent 350. As such, the surgeon does not need to adjust the controls of the electrosurgical generator "G" or take his/her focus and/or attention away from the patient and the surgical procedure being performed. In addition, in combination or alternatively, a status monitor may also be employed to provide visual and audible indications corresponding to the operational status of the generator "G". For example, one such status monitor is described in commonly owned U.S. Pat. No. 6,402,741 entitled "CURRENT AND STATUS MONITOR", the entire contents of which are hereby incorporated by reference herein.

While embodiments of electrosurgical instruments according to the present disclosure have been described herein it is not intended that the disclosure be limited there and the above description should be construed as merely exemplifications of preferred embodiments. Those skilled in the art will envision other modifications within the scope and spirit of the present disclosure.

What is claimed is:

1. An electrosurgical pencil, comprising:
   an elongated housing;
   an electrocautery blade supported within the housing and extending distally therefrom, the electrocautery blade being connected to a source of electrosurgical energy;
   an activation button supported on the housing;
   a transducer electrically connected between the activation button and the source of electrosurgical energy, the transducer being configured to transmit an electrical output signal to the electrosurgical energy source correlating to the movement of the activation button, the source of electrosurgical energy correspondingly supplying an amount of electrosurgical energy to the electrocautery blade dependant upon the electrical output signal; and
   a control pendent operatively coupled to the housing and electrically connected to the source of electrosurgical energy, the control pendent including at least one control knob operatively supported thereon, wherein the at least one control knob is configured and adapted to enable selection of a particular emission signal from the source of electrosurgical energy.

2. The electrosurgical instrument according to claim 1, wherein the at least one control knob is electrically connected to the activation button.

3. The electrosurgical instrument according to claim 2, wherein the at least one control knob is electrically connected to the source of electrosurgical energy.

4. The electrosurgical instrument according to claim 2, wherein the control pendent is configured and adapted to be removably attached to at least one of a user's wrist, a user's garment, and an operating table.

5. The electrosurgical instrument according to claim 4, wherein the control pendent includes at least one knob for selecting a function of the electrosurgical instrument and at least one other knob for selecting a power output of the source of electrosurgical energy.

6. An electrosurgical system, comprising:
   a source of electrosurgical energy; and
   an electrosurgical pencil connectable to the source of electrosurgical energy, the electrosurgical pencil including:
   an elongated housing;
   an electrocautery blade supported within the housing and extending distally from the housing, said electrocautery blade being connected to the source of electrosurgical energy;
   a single activation button supported on the housing, said activation button being movable from a first position to a plurality of subsequent positions in order to activate a plurality of therapeutic effects and to vary an amount of electrosurgical energy transmitted to the electrocautery blade; and
   a transducer electrically connected between the activation button and the source of electrosurgical energy, said transducer being configured to transmit a discrete electrical output signal to the electrosurgical energy source correlating to each of said plurality of subsequent positions of the activation button, the source of electrosurgical energy correspondingly supplying an amount of electrosurgical energy to the electrocautery blade dependant upon the discrete electrical output signal and at least one of said plurality of diverse therapeutic effects.

7. An electrosurgical system according to claim 6, wherein the activation button is configured to initiate transmission of the electrical output signal.

8. An electrosurgical system according to claim 7, wherein the activation button is configured for movement from a first position to a series of discrete, subsequent positions wherein each subsequent position corresponds to a specific amount of electrosurgical energy being transmitted to the electrocautery blade.

9. An electrosurgical system according to claim 7, wherein the transducer is a pressure-sensitive transducer.

10. An electrosurgical system according to claim 9, wherein the pressure transducer is configured to produce at least two output signals based upon the movement of the activation button.

11. An electrosurgical system according to claim 10, wherein one of the at least two signals produced by the pressure transducer transmits a signal to the electrosurgical generator corresponding to a cutting-type waveform and wherein the other of the at least two signals produced by the pressure transducer transmits a signal to the source of electrosurgical energy corresponding to a coagulating-type waveform.

12. An electrosurgical system according to claim 9, wherein the pressure transducer is configured to transmit a range of output signals to the source of electrosurgical energy in response to the position of the activation button, the range of output signals corresponding to a range of energy delivered from the source of electrosurgical energy to the electrocautery blade.

13. The electrosurgical system according to claim 6, wherein the activation button includes a slide-switch which is slidingly supported on the housing and is configured for selective movement along a slide path formed in the housing.

14. The electrosurgical system according to claim 13, wherein the transducer is configured to produce an output signal to the source of electrosurgical energy which corresponds to the movement of the slide-switch within the slide path of the housing.

15. The electrosurgical system according to claim 13, wherein the slide-switch transmits a range of output signals to the source of electrosurgical energy in response to the position of the slide-switch, the range of output signals varying from when the slide-switch is at a proximal-most position to when the slide switch is at a distal-most position.

16. The electrosurgical system according to claim 13, wherein the slide-switch is adapted to be depressed to initiate movement thereof and activation of the electrocautery blade.

17. An electrosurgical device, comprising:
   a single activation button movable from a first position to a plurality of subsequent positions in order to activate a plurality of diverse therapeutic effects and to vary an amount of electrosurgical energy transmitted by the electrosurgical device; and
   a transducer electrically connected between the activation button and a source of electrosurgical energy, said transducer being configured to transmit a discrete electrical output signal to the electro surgical energy source correlating to each of said plurality of subsequent positions of the activation button, the source of electrosurgical energy correspondingly supplying an amount of electrosurgical energy to the electrocautery blade dependant upon the discrete electrical output signal and at least one of said plurality of diverse therapeutic effects.

18. An electrosurgical device according to claim 17, wherein the activation button is configured for movement from a first position to a series of discrete, subsequent positions wherein each subsequent position corresponds to a specific amount of electrosurgical energy being transmitted by the electrosurgical device.

19. An electrosurgical device according to claim 18, wherein the transducer is configured to produce at least two output signals based upon the movement of the activation button.

20. An electrosurgical device according to claim 19, wherein one of the at least two signals produced by the pressure transducer transmits a signal to the electrosurgical generator corresponding to a cutting-type waveform and wherein the other of the at least two signals produced by the pressure transducer transmits a signal to the source of electrosurgical energy corresponding to a coagulating-type waveform.

21. An electrosurgical device according to claim 17, wherein the transducer is configured to transmit a range of output signals to the source of electrosurgical energy in response to the position of the activation button, the range of output signals corresponding to a range of energy emission from the source of electrosurgical energy to the electrosurgical device.

22. The electrosurgical device according to claim 17, wherein the activation button includes a slide-switch which is slidingly supported along a slide path formed in the device.

23. The electrosurgical device according to claim 22, wherein the transducer is configured to produce an output signal to the source of electrosurgical energy which corresponds to the movement of the slide-switch within the slide path.

24. The electrosurgical device according to claim 22, wherein the slide-switch transmits a range of output signals to the source of electrosurgical energy in response to the position of the slide-switch, the range of output signals varying from when the slide-switch is at a proximal-most position to when the slide switch is at a distal-most position.

25. The electrosurgical device according to claim 22, wherein the slide-switch is adapted to be depressed to initiate movement thereof and a transmission of electrosurgical energy.

26. A surgical device, comprising:
a housing having an activation switch disposed thereon, the activation switch adapted to couple to an electrosurgical energy source, the activation switch including a knob slidingly disposed within a guide channel defined within said housing; and
the activation switch being selectively moveable in a first direction within the guide channel to set a desired electrosurgical energy level and the activation switch being selectively moveable in a second direction to activate the electrosurgical energy source.

27. The surgical device according to claim 26, wherein the activation switch is operable to set the intensity level of electrosurgical energy before electrosurgical energy is activated.

28. The surgical device according to claim 26, wherein the knob is biased in an inactivated position.

29. The surgical device according to claim 26, wherein the guide channel includes a plurality of discreet positions, the knob being slideable between the plurality of discreet positions.

30. The surgical device according to claim 29, wherein tactile feedback is provided to a user when the knob is slid between the plurality of discreet positions on the guide channel.

31. The surgical device according to claim 26, wherein the device is an electrosurgical pencil.

32. A method for using a surgical device to administer electrosurgical energy to a patient, comprising the steps of:
providing a surgical device, including:
a housing having an activation switch disposed thereon, the activation switch adapted to couple to an electrosurgical energy source, the activation switch including a knob slidingly disposed within a guide channel defined within said housing; and
the activation switch being selectively moveable in a first direction within the guide channel to set a desired electrosurgical energy level and the activation switch being selectively moveable in a second direction to activate the electrosurgical energy source;
sliding the knob to set the intensity level of electrosurgical energy; and
depressing the knob to activate electrosurgical energy.

33. The method according to claim 32, wherein the activation switch is operable to set the intensity level of electrosurgical energy before electrosurgical energy is activated.

34. The method according to claim 32, wherein the guide channel includes a plurality of discreet positions, the knob being slideable between the plurality of discreet positions.

35. An electrosurgical system for performing electrosurgery on a patient, the electrosurgical system comprising:
an electrosurgical energy source that provides electrosurgical energy;
an active electrode which supplies electrosurgical energy to a patient;
an electrosurgical return electrode which returns electrosurgical energy to the electrosurgical energy source; and
a surgical device, including:
a housing having an activation switch disposed thereon, the activation switch adapted to couple to the electrosurgical energy source, the activation switch including a knob slidingly disposed within a guide channel defined within said housing; and
the activation switch being selectively moveable in a first direction within the guide channel to set a desired electrosurgical energy level and the activation switch being selectively moveable in a second direction to activate the electrosurgical energy source.

36. The electrosurgical system according to claim 35, wherein the activation switch is operable to set the intensity level of electrosurgical energy before electrosurgical energy is activated.

37. The electrosurgical system according to claim 35, wherein the guide channel includes a plurality of discreet positions, the knob being slideable between the plurality of discreet positions.

* * * * *